(12) United States Patent
Machida et al.

(10) Patent No.: US 10,328,740 B2
(45) Date of Patent: Jun. 25, 2019

(54) SLIDE TRAY

(71) Applicant: Sony Corporation, Tokyo (JP)

(72) Inventors: Yuuichi Machida, Kanagawa (JP); Yu Hirono, Tokyo (JP); Nobuhiro Hayashi, Kanagawa (JP); Takamichi Yamakoshi, Tokyo (JP)

(73) Assignee: Sony Corporation, Tokyo (JP)

( * ) Notice: Subject to any disclaimer, the term of this patent is extended or adjusted under 35 U.S.C. 154(b) by 634 days.

(21) Appl. No.: 14/420,923

(22) PCT Filed: Aug. 21, 2013

(86) PCT No.: PCT/JP2013/004930
§ 371 (c)(1),
(2) Date: Feb. 11, 2015

(87) PCT Pub. No.: WO2014/034048
PCT Pub. Date: Mar. 6, 2014

(65) Prior Publication Data
US 2015/0202910 A1 Jul. 23, 2015

(30) Foreign Application Priority Data
Aug. 29, 2012 (JP) .................. 2012-188897

(51) Int. Cl.
*B01L 9/00* (2006.01)
*B42F 7/10* (2006.01)
(Continued)

(52) U.S. Cl.
CPC .............. *B42F 7/10* (2013.01); *B01L 9/52* (2013.01); *B65D 1/36* (2013.01); *G02B 21/34* (2013.01);
(Continued)

(58) Field of Classification Search
CPC ................ B01L 9/52; B01L 2300/021; B01L 2300/024; B01L 2300/0822;
(Continued)

(56) References Cited

U.S. PATENT DOCUMENTS

| 4,819,804 A | 4/1989 | Levy |
| 2002/0079239 A1 | 6/2002 | Hrisinko |
| 2010/0065458 A1* | 3/2010 | Myers ...................... B01L 9/52 |
| | | 206/459.1 |

FOREIGN PATENT DOCUMENTS

| JP | 07-291386 | 11/1995 |
| JP | 2004-029012 | 1/2004 |
| JP | 2004-244083 | 9/2004 |

OTHER PUBLICATIONS

International Search Report issued in connection with International Patent Application No. PCT/JP2013/004930, dated Nov. 5, 2013. (2 pages).

* cited by examiner

*Primary Examiner* — Anthony D Stashick
*Assistant Examiner* — James M Van Buskirk
(74) *Attorney, Agent, or Firm* — K&L Gates LLP (57) ABSTRACT

[Object] To provide a slide tray having excellent practicality, convenience, and the like.
[Solving Means] A slide tray includes a slide tray body having a first surface on which one or more slides can be mounted, and one or more first convex portions that protrude from the first surface of the slide tray body and set an area in which paper sheets can be mounted on the first surface while being held from one side in a first axis direction of two axis directions orthogonal to each other on the first surface.

6 Claims, 4 Drawing Sheets

(51) Int. Cl.
*B65D 1/36* (2006.01)
*G01N 1/31* (2006.01)
*G02B 21/34* (2006.01)
*G01N 35/04* (2006.01)

(52) U.S. Cl.
CPC ...... *B01L 2300/0822* (2013.01); *G01N 1/312* (2013.01); *G01N 2035/0498* (2013.01)

(58) Field of Classification Search
CPC ......... B01L 2200/028; B01L 2300/022; G02B 21/34; B42F 7/10; B65D 1/36; G01N 2035/0498; G01N 1/312
USPC ..... 206/232, 456, 425, 459.1, 509, 561, 563
See application file for complete search history.

SLIDE TRAY

CROSS REFERENCES TO RELATED APPLICATIONS

The present application is a national stage of International Application No. PCT/JP2013/004930 filed on Aug. 21, 2013 and claims priority to Japanese Patent Application No. 2012-188897 filed on Aug. 29, 2012, the disclosure of which is incorporated herein by reference.

BACKGROUND

The present technology relates to a slide tray that accommodates slides.

In the fields of medical care, pathologies, and the like, a slide tray (also referred to as "mappe") that accommodates a plurality of optical microscope slide glasses arranged in matrix (hereinafter, simply referred to as "slides") onto which sections of biological cells, tissues, organs, and the like are mounted is widely known (see, for example, Patent Document 1). Such slide trays are stacked for storage in many cases. However, in the case where the slide trays are not stacked in line, and the like, there is a possibility that the slide trays collapse. Additionally, there are many cases where the slide trays are stacked with a piece of paper such as a medical record intervening between the slide trays. If a piece of paper such as a medical record intervenes between the slide trays and protrudes from the slide trays, this makes it more difficult to stack the plurality of slide trays in line. Additionally, if the piece of paper protrudes from the slide trays, this makes it difficult to visually recognize labels and the like attached to or described on side surfaces of the slide trays. As described above, there is still room for improvement regarding practicality, convenience, and the like of the slide tray.

Patent Document 1: Japanese Patent Application Laid-open No. Hei 07-291386

SUMMARY

Problem to be Solved by the Invention

In view of the circumstances as described above, it is an object of the present technology to provide a slide tray having excellent practicality, convenience, and the like.

Means for Solving the Problem

To solve the problems described above, according to an embodiment of the present invention, there is provided a slide tray including: a slide tray body having a first surface on which one or more slides can be mounted; and one or more first convex portions that protrude from the first surface of the slide tray body and set an area in which paper sheets can be mounted on the first surface while being held from one side in a first axis direction of two axis directions orthogonal to each other on the first surface.

The slide tray further includes a first concave portion that is provided to a second surface and provided to correspond to each of the one or more first convex portions, the second surface being an opposite surface of the first surface of the slide tray body.

The area is set by the one or more first convex portions and a part of the other side in the first axis direction of the first surface.

The slide tray further includes one or more second convex portions to set an area in which paper sheets can be mounted on the first surface while being held from at least one side in a second axis direction of the two axis directions.

An end portion of each of the one or more first convex portions, the end portion facing the area, is positioned in alignment in the second axis direction, and an end portion of each of the one or more second convex portions, the end portion facing the area, is positioned in alignment in the first axis direction.

The slide tray further includes a second concave portion that is provided to the second surface of the slide tray body and provided to correspond to each of the one or more second convex portions.

Effect of the Invention

According to the present technology, it is possible to provide a slide tray having excellent practicality, convenience, and the like.

Additional features and advantages are described herein, and will be apparent from the following Detailed Description and the figures.

DETAILED DESCRIPTION

Hereinafter, an embodiment of the present technology will be described with reference to the drawings.

Embodiment

1. Structure of Slide Tray

Figure 1:
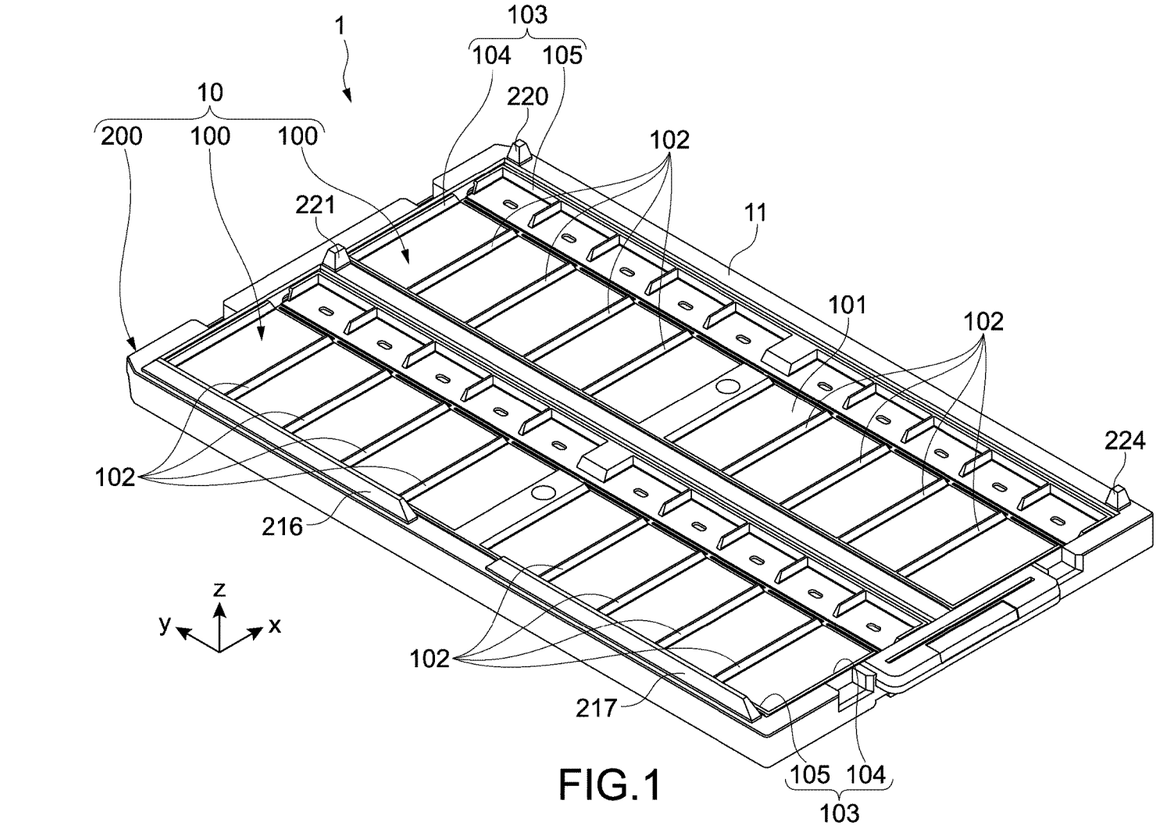
FIG. 1 is a perspective view of a slide tray according to an embodiment.

FIG. 1 is a perspective view of a slide tray 1 according to an embodiment.

The slide tray 1 includes one or more slide accommodation portions 100 and 100 and a frame 200. The one or more slide accommodation portions 100 and 100 and the frame 200 form a slide tray body 10. The one or more slide accommodation portions 100 and 100 are positioned on an upper surface 11 (first surface) of the slide tray body 10. The upper surface 11 of the slide tray body 10 is a rectangle, for example. The one or more slide accommodation portions 100 and 100 are each capable of accommodating a plurality of slides (not shown) mounted thereon. The frame 200 sections, encloses, and constrains the one or more slide accommodation portions 100 and 100. The height of the frame 200 is larger than the height of the slide accommodation portion 100.

It should be noted that in the specification, the "rectangle" refers not only to an exact rectangle (i.e., square in which four corners are right angles and two opposing sides have the same length) but also to a practically rectangular shape. For example, even when an angle formed by two orthogonal sides is round or notched, the shape is referred to as a "rectangle". Moreover, even when an arbitrary side has irregularities, the shape is referred to as a "rectangle" as long as it has a rectangular impression dominantly on the whole.

[1.1. Structure of Slide Accommodation Portion]

The one or more slide accommodation portions 100 and 100 have the same structure. So, in the descriptions below, unless there is a need to distinguish the one or more slide accommodation portions 100 and 100 from one another, the slide accommodation portions 100 and 100 will be referred to as a "slide accommodation portion 100", and description will be given on a single slide accommodation portion 100.

The slide accommodation portion 100 includes a mount plate 101, a plurality of partitions 102, and an outer frame 103. A plurality of slides can be mounted adjacently on the mount plate 101.

The plurality of partitions 102 each protrude from the mount plate 101 in a direction orthogonal to the mount plate 101, section the mount plate 101 on which the plurality of slides are mounted adjacently, and separate the plurality of slides from one another. Specifically, the plurality of partitions 102 section the mount plate 101 such that the plurality of slides can be arranged in parallel in one line in a state where long sides of the plurality of slides as rectangular thin plates are adjacent to each other and one surface of each slide entirely comes into contact with the mount plate 101. The plurality of partitions 102 restrict the longitudinal movements of the slides mounted on the mount plate 101.

It should be noted that in the description hereinafter, a longitudinal direction of the plurality of slides (short side direction of slide) on the mount plate 101 is referred to as a Y direction (second axis direction), a direction orthogonal to the Y direction (long side direction of slide) on the mount plate 101 is referred to as an X direction (first axis direction), and a direction orthogonal to the mount plate 101 (thickness direction of slide) is referred to as a Z direction.

The outer frame 103 surrounds the circumference of the mount plate 101 and protrudes from the mount plate 101 in the Z direction. The Z-direction height of the outer frame 103 from the mount plate 101 and that of the plurality of partitions 102 from the mount plate 101 are the same. More specifically, the Z-direction height of the outer frame 103 and that of the plurality of partitions 102 are set to be larger than a thickness of a general slide. The outer frame 103 includes a pair of first outer frames 104 and 104 whose longitudinal direction extends in the X direction and a pair of second outer frames 105 and 105 whose longitudinal direction extends in the Y direction. The pair of first outer frames 104 and 104 restrict Y-direction movements of the slides positioned at both ends in the longitudinal direction. The pair of second outer frames 105 and 105 restrict X-direction movements of the plurality of slides. As described above, the slides are arranged such that four sides thereof come into contact with the outer frame 103 and the partitions 102 as a partition portion. In this state, the outer frame 103 and the partitions 102 as the partition portion restrict movements of the slides.

[1.2. Plurality of Convex Portions]

Figure 2:
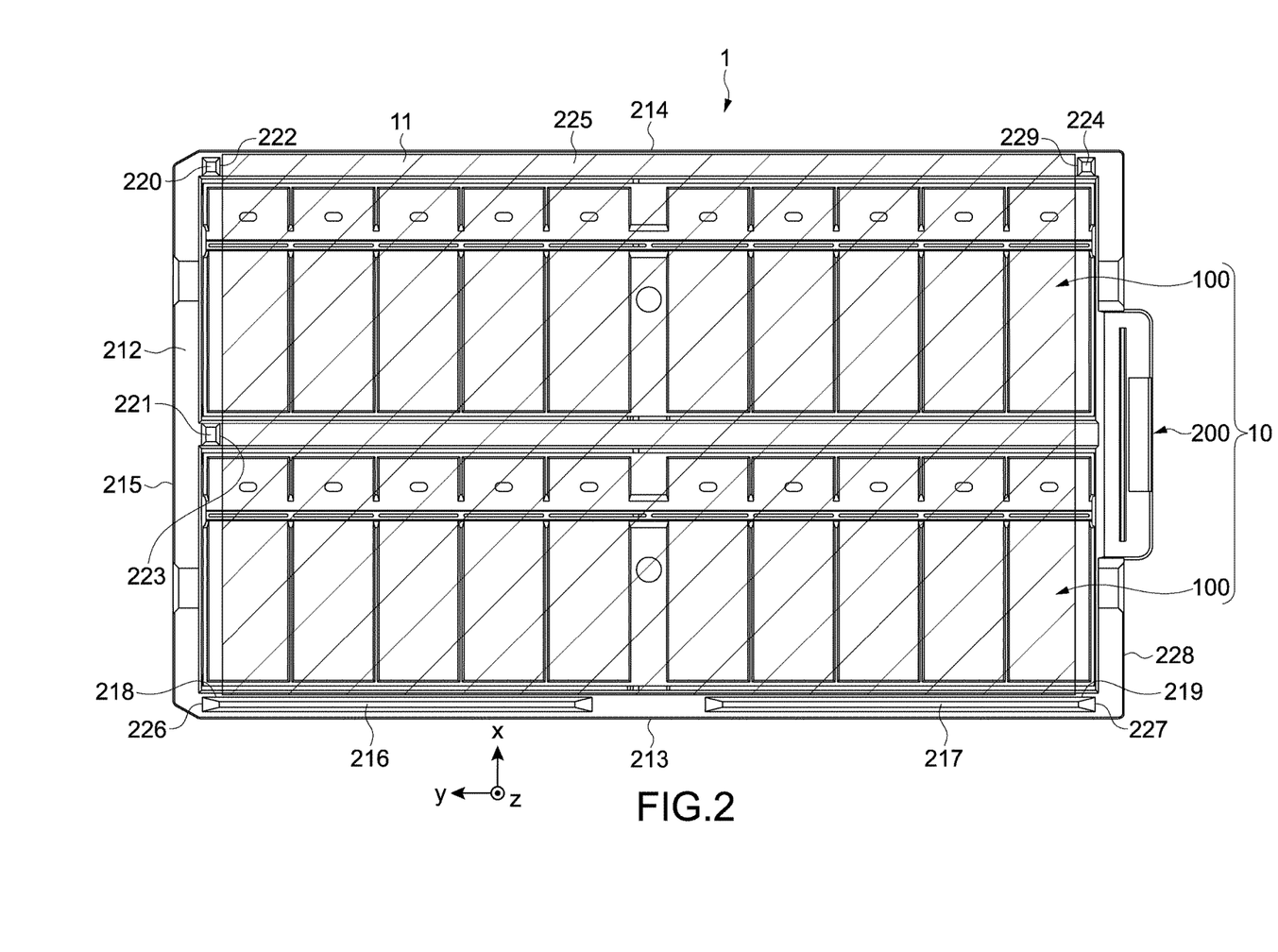
FIG. 2 is a top view of the slide tray.

FIG. 2 is a top view of the slide tray 1.

A plurality of convex portions that protrude in the Z direction are provided on the upper surface 11 (first surface) of the slide tray body 10. Specifically, a plurality of convex portions that protrude in the Z direction are provided on an upper surface 212 of the frame 200. More specifically, in this embodiment, a first long-side convex portion 216, a second long-side convex portion 217, a first short-side convex portion 220, a second short-side convex portion 221, and a third short-side convex portion 224 are provided.

The first long-side convex portion 216 and the second long-side convex portion 217 are provided along one long side 213 of the rectangular upper surface 11 of the slide tray body 10, the long side 213 extending in the Y direction. More specifically, an end portion 218 of the first long-side convex portion 216, which faces the other long side 214, and an end portion 219 of the second long-side convex portion 217, which faces the long side 214, are positioned in alignment in the Y direction.

The first short-side convex portion 220 and the second short-side convex portion 221 are provided along one short side 215 of the rectangular upper surface 11 of the slide tray body 10, the short side 215 extending in the X direction. More specifically, an end portion 222 of the first short-side convex portion 220, which faces the other short side 228, and an end portion 223 of the second short-side convex portion 221, which faces the short side 228, are positioned in alignment in the X direction.

The third short-side convex portion 224 is provided along the short side 228 of the rectangular upper surface 11 of the slide tray body 10. More specifically, an end portion 229 of the third short-side convex portion 224, which faces the short side 215, is positioned in alignment in the X direction.

An area (hatched area) set (sectioned) by the end portion 218 of the first long-side convex portion 216, the end portion 219 of the second long-side convex portion 217, the end portion 222 of the first short-side convex portion 220, the end portion 223 of the second short-side convex portion 221, the end portion 229 of the third short-side convex portion 224, and a part of the long side 214 is assumed as a convex portion prohibition area 225. The convex portion prohibition area 225 is an area in which a convex portion protruding in the Z direction is prohibited to be provided.

Figure 3:
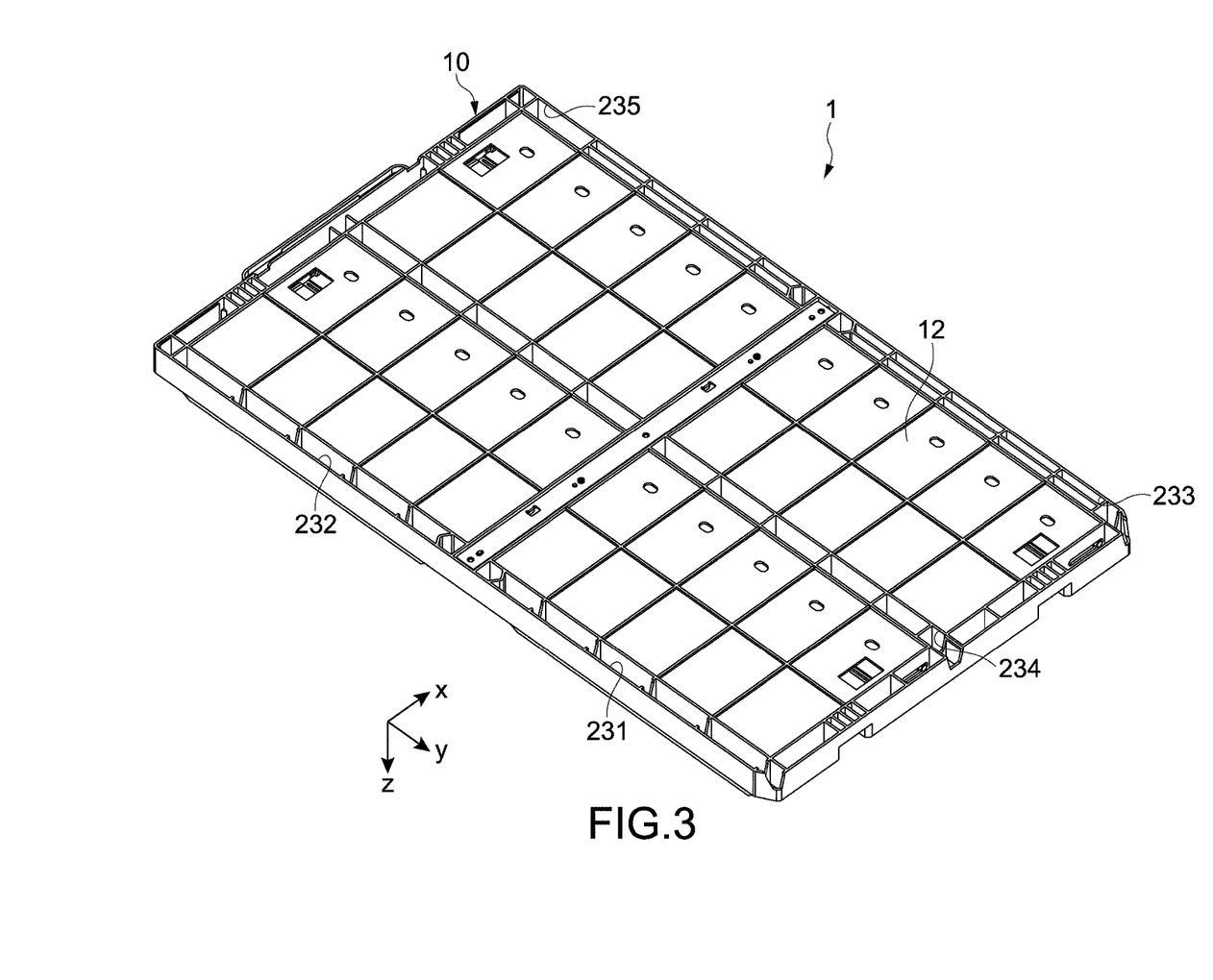
FIG. 3 is a bottom perspective view of the slide tray.

FIG. 3 is a bottom perspective view of the slide tray 1.

At least concave portions that are recessed in the Z direction are provided to a lower surface 12 (second surface) of the slide tray body 10 so as to correspond to at least the first long-side convex portion 216, the second long-side convex portion 217, the first short-side convex portion 220, the second short-side convex portion 221, and the third short-side convex portion 224. In this embodiment, a first long-side concave portion 231 (first concave portion) to face the first long-side convex portion 216, and a second long-side concave portion 232 (first concave portion) to face the second long-side convex portion 217 are provided to the lower surface 12 of the slide tray body 10. Further, a first short-side concave portion 233 (second concave portion) to face the first short-side convex portion 220, and a second short-side concave portion 234 (second concave portion) to face the second short-side convex portion 221 are provided to the lower surface 12 of the slide tray body 10. Furthermore, a third short-side concave portion 235 (third concave portion) to face the third short-side convex portion 224 is provided to the lower surface 12 of the slide tray body 10. The Z-direction depth of each of the concave portions 231, 232, 233, 234, and 235 is equal to or larger than the Z-direction protrusion length of each of the convex portions 216, 217, 220, 221, and 224, respectively. More specifically, the concave portions 231, 232, 233, 234, and 235 are capable of fully accommodating convex portions having the same shape as the opposing convex portions 216, 217, 220, 221, and 224, respectively.

2. Slide Tray Stack

The plurality of slide trays 1 each including the frame 200 having the structure as described above can be stacked in the Z direction. Specifically, the first and second long-side convex portions 216 and 217 of one slide tray 1 (lower slide tray 1) are fit in the first and second long-side concave portions 231 and 232 of another slide tray 1 (upper slide tray 1), respectively. The first, second, and third short-side convex portions 220, 221, and 224 of the one slide tray 1 (lower slide tray 1) are fit in the first, second, and third short-side concave portions 233, 234, and 235 of the other slide tray 1 (upper slide tray 1), respectively. In this case, the lower surface 12 of the slide tray body 10 of the upper slide tray 1 comes into contact with the upper surface 11 of the slide tray body 10 of the lower slide tray 1. As a result, the upper slide tray 1 is held horizontally by the lower slide tray 1. Here, the Z-direction height of the frame 200 is equal to or larger than that of the slide accommodation portion 100. So, even when a plurality of slide trays 1 are stacked with the slides being accommodated in the slide accommodation portion 100, the upper slide tray 1 does not interfere with the slides accommodated in the lower slide tray 1.

Further, the slide trays 1 can be stacked with paper sheets such as medical records being mounted in the convex portion prohibition area 225 and intervening between the slide trays 1. As described above, in the slide accommodation portion 100, the Z-direction height of the outer frame 103 from the mount plate 101 and the Z-direction height of the plurality of partitions 102 from the mount plate 101 are the same. So, the lower surface of a piece of paper intervening between the slide trays 1 is horizontally supported by the slide accommodation portion 100 of the lower slide tray 1. On the other hand, the upper surface of the piece of paper is horizontally supported by the lower surface of the upper slide tray 1.

Furthermore, the Z-direction height of the outer frame 103 and the plurality of partitions 102 of the slide accommodation portion 100 is set to be larger than the thickness of a general slide. So, when the plurality of slide trays 1 are stacked with the slides being accommodated in the slide accommodation portion 100 and with a piece of paper intervening between the slide trays 1, the piece of paper is horizontally supported by the outer frame 103 and the plurality of partitions 102 located at positions higher than the upper surfaces of the slides. This prevents the piece of paper from interfering with the slides accommodated in the lower slide tray 1.

As described above, the plurality of convex portions 216, 217, 220, 221, and 224 and the plurality of concave portions 231, 232, 233, 234, and 235 are fit in each other, respectively. As a result, at least the following effects are obtained.
(1) The plurality of convex portions 216, 217, 220, 221, and 224 and the plurality of concave portions 231, 232, 233, 234, and 235 each become a stacking guide so that the plurality of slide trays 1 can be easily stacked in alignment in the three XYZ directions.
(2) Since the plurality of convex portions 216, 217, 220, 221, and 224, which are provided to the three sides 213, 215, and 228, are fit in the plurality of concave portions 231, 232, 233, 234, and 235, respectively, fitting is secure. Consequently, the slide trays 1 can be stacked with high stability, and thus there is less possibility of collapsing.

3. Specific Example of Size of Slide Tray

Figure 4:
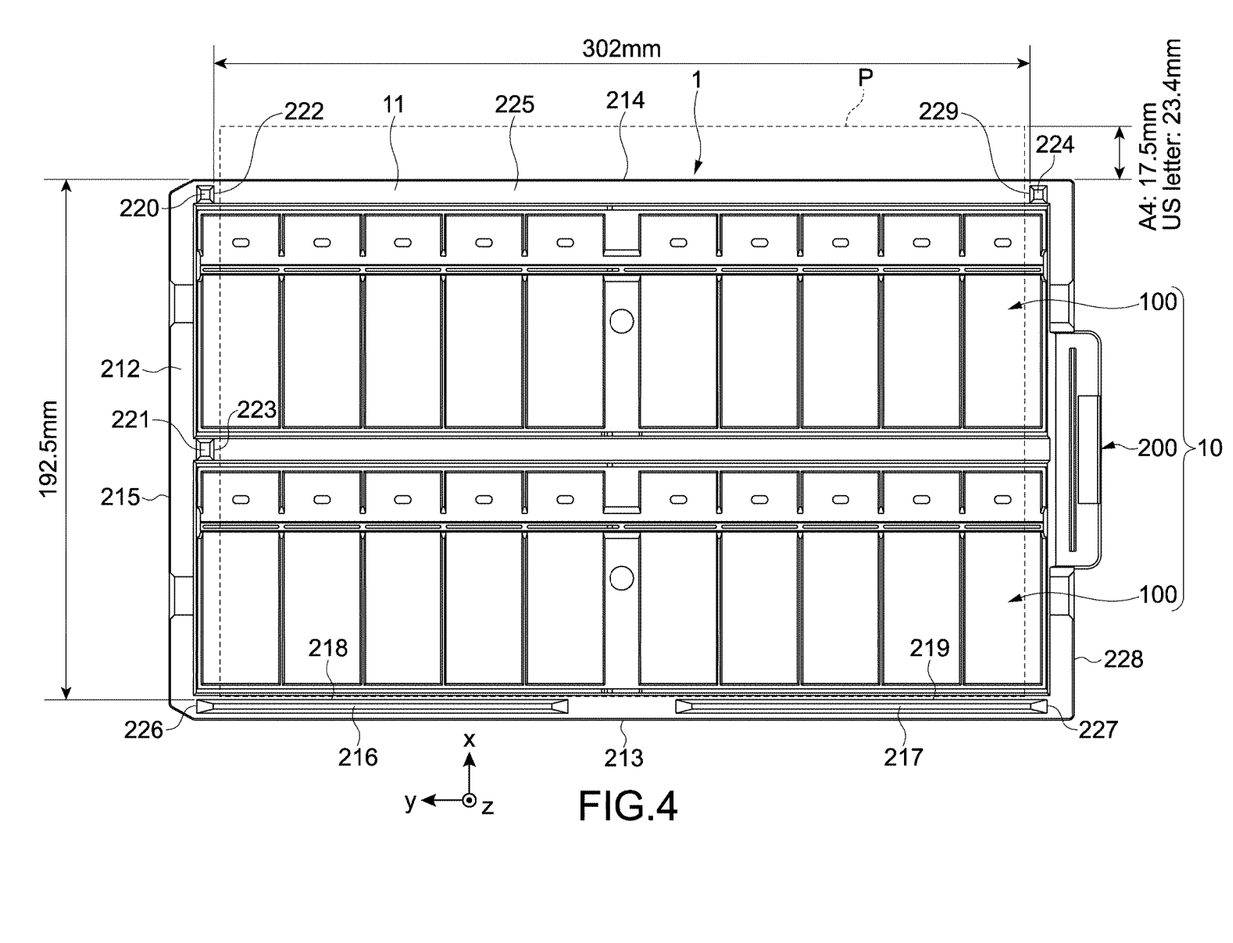
FIG. 4 is a top view of the slide tray, for describing a specific example of a size of the slide tray.

FIG. 4 is a top view of the slide tray 1, for describing a specific example of the size of the slide tray 1.

Specific examples of the size of the slide tray 1 include the following size. Specifically, a distance in the X direction from the end portion 218 of the first long-side convex portion 216, which faces the long side 214, and the end portion 219 of the second long-side convex portion 217, which faces the long side 214, to the second side 214 is 192.5 mm. A distance in the Y direction from the end portion 222 of the first short-side convex portion 220, which faces the short side 228, to the end portion 229 of the third short-side convex portion 224, which faces the short side 215, is 302 mm. In other words, the length of the convex portion prohibition area 225 in the X direction is 192.5 mm and the length thereof in the Y direction is 302 mm.

It is assumed that a plurality of slide trays 1 are stacked, with a piece of paper P (paper sheets such as medical records) being mounted in the convex portion prohibition area 225 and intervening between the slide trays 1. For example, it is assumed that a piece of paper with A4 size (210 mm×297 mm), which is thought to be used most frequently, is mounted in the convex portion prohibition area 225, with a short side of the piece of paper becoming parallel to the X direction and a long side thereof becoming parallel to the Y direction and the piece of paper intervening between the slide trays 1. The long side (297 mm) of the piece of paper is shorter by 5 mm than the distance in the Y direction (302 mm) from the first short-side convex portion 220 and the second short-side convex portion 221 to the third short-side convex portion 224. So, the piece of paper is held by the first short-side convex portion 220, the second short-side convex portion 221, and the third short-side convex portion 224 from both sides in the Y direction, and the movement of the piece of paper is restricted. Thus, the piece of paper is positioned in the Y direction without rotation and the like on the slide tray 1.

Further, one long side of the piece of paper mounted in the convex portion prohibition area 225 is caused to come into contact with a side surface 218 of the first long-side convex portion 216 and a side surface 219 of the second long-side convex portion 217. Thus, the piece of paper is held by the first long-side convex portion 216 and the second long-side convex portion 217 from one side in the X direction, and the movement of the piece of paper is restricted. Thus, the piece of paper is positioned in the X direction. On the other hand, a short side (210 mm) of the piece of paper is longer by 17.5 mm than the distance (192.5 mm) from the side surface 218 of the first long-side convex portion 216 and the side surface 219 of the second long-side convex portion 217 to the second side 214. So, the piece of paper protrudes from the second side 214 of the frame 200 by 17.5 mm. Since the amount of protrusion is only 17.5 mm with respect to the entire paper width (210 mm), even when this part does not intervene between the slide trays 1, there is less possibility that the protruding portion is deformed or the piece of paper slips off from the slide tray 1 due to the deformation. Further, for a piece of paper with A4 size, a part of the paper protrudes inevitably, and thus whether or not the piece of paper intervenes can be visually recognized at a glance.

For example, it is assumed that a piece of paper with US letter size (215.9 mm×279.4 mm), which is thought to be used second most frequently after the A4 size, is mounted in the convex portion prohibition area 225, with a short side of the piece of paper becoming parallel to the X direction and a long side thereof becoming parallel to the Y direction and the piece of paper intervening between the slide trays 1. The long side (279.4 mm) of the piece of paper is shorter by 22.6 mm than the distance (302 mm) from the first short-side convex portion 220 and the second short-side convex portion 221 to the third short-side convex portion 224. So, the piece of paper is held by the first short-side convex portion 220, the second short-side convex portion 221, and the third short-side convex portion 224 from both sides in the Y direction, and the movement of the piece of paper is restricted. Thus, the piece of paper is positioned without rotation and the like on the slide tray 1.

Further, one long side of the piece of paper mounted in the convex portion prohibition area 225 is caused to come into contact with a side surface 218 of the first long-side convex portion 216 and a side surface 219 of the second long-side convex portion 217. Thus, the piece of paper is held by the first long-side convex portion 216 and the second long-side convex portion 217 from one side in the X direction, and the movement of the piece of paper is restricted. Thus, the piece of paper is positioned in the X direction. On the other hand, a short side (215.9 mm) of the piece of paper is longer by 23.4 mm than the distance (192.5 mm) from the side surface 218 of the first long-side convex portion 216 and the side surface 219 of the second long-side convex portion 217 to the second side 214. So, the piece of paper protrudes from the second side 214 of the frame 200 by 23.4 mm. Since the amount of protrusion is only 23.4 mm with respect to the entire paper width (215.9 mm), even when this part does not intervene between the slide trays 1, there is less possibility that the protruding portion is deformed or the piece of paper slips off from the slide tray 1 due to the deformation. Further, for a piece of paper with US letter size, a part of the paper protrudes inevitably, and thus whether or not the piece of paper intervenes can be visually recognized at a glance.

When the slide tray 1 has the size as described above, the movement of a piece of paper with a predetermined size is restricted from three directions by the plurality of convex portions 216, 217, 220, 221, and 224 provided along the three sides 213, 215, and 228. With this, at least the following effects are obtained.

(1) Since a piece of paper protrudes exclusively in the second side 214 of the frame 200, whether or not the piece of paper intervenes can be visually recognized at a glance.
(2) Since the piece of paper does not protrude from at least three sides of the slide tray 1, if labels and the like are attached or described on the side surfaces of the slide tray 1 that correspond to those three sides, the visibility of labels is prevented from being reduced.
(3) Since the piece of paper protrudes from the slide tray 1, when a plurality of stacked slide trays 1 are set in a scanner apparatus or the like, the piece of paper is prevented from being left therein.

4. Effects

Hereinabove, according to the present technology, it is possible to use the plurality of convex portions 216, 217, 220, 221, and 224 as a stacking guide of the plurality of slide trays 1 and simultaneously as a guide of a piece of paper that intervenes between the plurality of slide trays 1.

<Others>
It should be noted that the present technology can have the following structures.
(1) A slide tray, including:
a slide tray body having a first surface on which one or more slides can be mounted; and
one or more first convex portions that protrude from the first surface of the slide tray body and set an area in which paper sheets can be mounted on the first surface while being held from one side in a first axis direction of two axis directions orthogonal to each other on the first surface.
(2) The slide tray according to (1) above, further including a first concave portion that is provided to a second surface and provided to correspond to each of the one or more first convex portions, the second surface being an opposite surface of the first surface of the slide tray body.
(3) The slide tray according to (1) or (2) above, in which the area is set by the one or more first convex portions and a part of the other side in the first axis direction of the first surface.
(4) The slide tray according to any one of (1) to (3) above, further including one or more second convex portions to set an area in which paper sheets can be mounted on the first surface while being held from at least one side in a second axis direction of the two axis directions.
(5) The slide tray according to any one of (1) to (4) above, in which
an end portion of each of the one or more first convex portions, the end portion facing the area, is positioned in alignment in the second axis direction, and
an end portion of each of the one or more second convex portions, the end portion facing the area, is positioned in alignment in the first axis direction.
(4) The slide tray according to any one of (6) to (5) above, further including a second concave portion that is provided to the second surface of the slide tray body and provided to correspond to each of the one or more second convex portions.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF REFERENCE NUMERALS

1 slide tray
10 slide tray body
100 slide accommodation portion
200 frame
216 first long-side convex portion
217 second long-side convex portion
220 first short-side convex portion
221 second short-side convex portion
224 third short-side convex portion
225 convex portion prohibition area
231 first long-side concave portion
232 second long-side concave portion
233 first short-side concave portion
234 second short-side concave portion
235 third short-side concave portion

The invention claimed is:
1. A slide tray, comprising:
a slide tray body having a first surface on which one or more slides are capable of being mounted;
and one or more first convex portions that protrude from the first surface of the slide tray body and set an area in which paper sheets are mountable on the first surface while being held from one side in a first axis direction of two axis directions orthogonal to each other on the first surface,
wherein the one or more first convex portions include at least two short-side convex portions provided on a long side of the slide tray body and another long-side convex portion provided on another long side of the slide tray body, and the at least two short-side convex portions are separated from each other with a convex portion prohibition area on the long side of the slide tray body between the two short convex portions and wherein the convex portion prohibition area is larger than the long-side convex portion.

2. The slide tray according to claim 1, further comprising a first concave portion that is provided to a second surface and provided to correspond to each of the first convex portions, the second surface being an opposite surface of the first surface of the slide tray body.

3. The slide tray according to claim 2, wherein
the area is set by the first convex portions and a part of the other side in the first axis direction of the first surface.

4. The slide tray according to claim 3, further comprising one or more second convex portions to set an area in which paper sheets can be mounted on the first surface while being held from at least one side in a second axis direction of the two axis directions.

5. The slide tray according to claim 4, wherein
an end portion of each of the first convex portions, the end portion facing the area, is positioned in alignment in the second axis direction, and
an end portion of each of the one or more second convex portions, the end portion facing the area, is positioned in alignment in the first axis direction.

6. The slide tray according to claim 5, further comprising a second concave portion that is provided to the second surface of the slide tray body and provided to correspond to each of the one or more second convex portions.

* * * * *